(12) United States Patent
Brady et al.

(10) Patent No.: US 8,618,063 B2
(45) Date of Patent: Dec. 31, 2013

(54) METHOD FOR TREATING A SYNUCLEINOPATHY

(75) Inventors: Scott Thomas Brady, Chicago, IL (US); Gerardo Andres Morfini, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 971 days.

(21) Appl. No.: 12/099,947

(22) Filed: Apr. 9, 2008

(65) Prior Publication Data

US 2009/0258814 A1 Oct. 15, 2009
US 2010/0105601 A2 Apr. 29, 2010

(51) Int. Cl.
*A61K 38/00* (2006.01)
*A61K 38/55* (2006.01)

(52) U.S. Cl.
USPC .......... 514/20.3; 514/7.5; 514/13.5; 514/17.7

(58) Field of Classification Search
None
See application file for complete search history.

(56) References Cited

U.S. PATENT DOCUMENTS

| 6,100,254 A * | 8/2000 | Budde et al. | 514/221 |
| 2003/0073632 A1 | 4/2003 | Ciaccia et al. | 514/12 |
| 2004/0014721 A1 * | 1/2004 | Hensley et al. | 514/64 |
| 2004/0176313 A1 | 9/2004 | Mercken et al. | 514/44 |

OTHER PUBLICATIONS

Morfini 2006 (Journal of Neurochemistry 96(Suppl 1):144).*
Auluck 2002 (Nature Medicine 8(11):1185-1186).*
Shen 2005 Journal of Biological Chemistry 280:39962-39969.*
Nishikawa 1997 Journal of Biological Chemistry 272:952-960.*
Beffert et al., "Reelin-mediated signaling locally regulates protein kinase B/Akt and glycogen synthse kinase 3β", J Biol Chem 2002 277(51):49958-49964.
Beffert et al., "Reelin and cyclin-dependent kinase 5-dependent signals cooperate in regulating neuronal migration and synaptic transmission", J Neuroscience 2004 24(8):1897-1906.
Morfini et al., "1-methyl-4-phenylpyridinium affects fast axonal transport by activationo f caspase and protein kinase C", Proc Natl Acad Sci USA 2007 104(7):2442-2447.

* cited by examiner

*Primary Examiner* — Jeffrey Stucker
*Assistant Examiner* — Adam M Weidner
(74) *Attorney, Agent, or Firm* — Licata & Tyrrell, P.C.

(57) ABSTRACT

The present invention relates to methods for restoring fast axonal transport in a cell which expresses a pathological synuclein protein and for treating a synucleinopathy using a Protein Kinase C mu or Src-Family Tyrosine Kinase inhibitor.

3 Claims, 9 Drawing Sheets

SEQUENCE LISTING

<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

```
Arg Arg Pro Ser Tyr Arg Lys
1               5

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide

<400> SEQUENCE: 2

Pro Leu Ala Arg Thr Leu Ser Val Ala Gly Leu Pro Gly Lys Lys
1               5                   10                  15
```

US 8,618,063 B2

METHOD FOR TREATING A SYNUCLEINOPATHY

INTRODUCTION

This invention was made with government support under Grant Nos. NS23868, NS23320, NS41170 and NS43408 awarded by the National Institute of Neurological Disorders and Stroke. The U.S. Government has certain rights in this invention.

BACKGROUND OF THE INVENTION

Parkinson's disease is a progressive neurological disorder due to a dying back neuropathy of axons projecting to the striatum from the substantia nigra. When ≈80% of synapses from nigral dopaminergic neurons are no longer functional, the shortage of dopamine in the striatum causes the movement defects that characterize Parkinson's disease. Typically, Parkinson's disease initially presents as tremor in a limb, especially when at rest. The tremor often begins on one side of the body, frequently in one hand. As the disease progresses, other common symptoms include slow movement (bradykinesia), a shuffling gait, and a stooped posture, progressing eventually to an inability to move (akinesia) and rigid limbs. People with Parkinson's disease often show reduced facial expressions and speak in a soft voice. As loss of neurons progresses, the disease may cause depression, personality changes, dementia, sleep disturbances, speech impairments or sexual difficulties. The severity of Parkinson's disease symptoms worsens over time and available treatments fail to stop or slow this progression.

Neuropathology in idiopathic Parkinson's disease is characterized by the presence of Lewy Bodies (LB) and filaments along with loss of nigral dopaminergic neurons. However, LB and Lewy neurites (LN) appear in a variety of brain regions, in some cases before significant involvement of nigral neurons. LB/LN develop when α-synucleins form filamentous aggregates in affected cells (Duda, et al. (2000) *J. Neurosci. Res.* 61:121-127; Spillantini & Goedert (2000) *Ann. NY Acad. Sci.* 920:16-27). The earliest detectable LB lesions are in the dorsal motor nucleus of the vagus and medulla oblongata regions like the locus coeruleus (Braak, et al. (2004) *Cell Tissue Res.* 318:121-34). When LB/LN pathology is restricted to these regions, there are no symptoms. Subsequently, LB appear in midbrain, particularly the substantia nigra where appearance of substantial LB/LN is associated with development of motor symptoms (Braak, et al. (2004) supra; Fearnley & Lees (1991) *Brain* 114(Pt 5):2283-301). In advanced stages of Parkinson's disease, substantia nigral pathology becomes more severe and neurons in the neocortex are affected as well (Braak, et al. (2004) supra). Contrary to conventional wisdom, a wide variety of neurons in various brain regions are affected by LB/LN pathology. Affected neurons are not necessarily dopaminergic, nor are all dopaminergic neurons affected, but neurons predisposed to LB pathology share some common features (Braak, et al. (2004) supra) Typically, these are projection neurons with long, non-myelinated or minimally myelinated axons. Such neurons are frequently associated with motor areas of the brain. Clinical symptoms most commonly associated with Parkinson's disease are clearly associated with damage to nigral dopaminergic neurons projecting to striatum, advancing to other symptoms including cognitive problems as cortical neurons are increasingly affected (Braak, et al. (2003) *Neurobiol. Aging* 24:197-211; Galvin, et al. (2001) *Arch. Neurol.* 58:186-190).

Treatments for Parkinson's disease have relied primarily on a strategy of enhancing the effects of surviving dopaminergic pathways, following different strategies to increase dopamine levels, use of dopamine agonists and inhibitors of dopamine degradation. There have also been attempts to replacement of dopaminergic neurons using stem cell technologies. As interest in neuroprotective strategies has increased, a variety of approaches have been tried, including antioxidants, anticholinergics, antiapoptotic compounds, neuropeptides, and neurotrophins (Andersen, et al. (2001) *Sci. Aging Knowledge Environ.* 2001:re1). Although some of these approaches ameliorate clinical symptoms to some extent or enhance the effectiveness of L-DOPA treatments, none have significantly altered the course of the disease. For example, GDNF administration showed considerable potential in animal studies (Burton, et al. (2003) *Gene Ther.* 10:1721-7) and advanced into clinical trials, but GDNF trials were discontinued for lack of efficacy in humans, although anecdotal evidence of improvement exists.

Parkinson's disease symptoms appear when the loss of dopaminergic terminals in the striatum reaches a critical point (Andersen, et al. (2001) supra; Dauer & Przedborski (2003) *Neuron* 39:889-909). Approximately 95% of Parkinson's disease cases are sporadic with an undetermined fraction resulting from environmental factors (Bossy-Wetzel, et al. (2004) *Nat. Med.* 10:S2-S9). Mutations in four to eight genes can lead to familial Parkinson's disease including genes of known and unknown function (Cookson (2005) *Annu. Rev. Biochem.* 74:29-52). Both autosomal dominant (PARK1, 3-5) and recessive (PARK2, 6-7) forms exist, with variable onset, rate of progression and degree of LB pathology (Cookson (2005) supra). All of these mutations are rare and together account for only 5% of Parkinson's disease cases.

The first described mutations associated with familial Parkinson's disease were in α-synuclein, where point mutations at Ala30Pro, Ala53Thr, or Glu46Lys lead to an autosomal dominant familial Parkinson's disease generally with prominent LB (Cookson (2005) supra). α-Synuclein is a 140 amino acid residue polypeptide of unknown function, predominantly expressed in neurons and enriched in presynaptic terminals (Spillantini & Goedert (2000) supra). Although α-synuclein has no defined solution structure, it can form filamentous aggregates that coalesce to form LB in vivo (Spillantini & Goedert (2000) supra; Cookson (2005) supra) and recombinant α-synuclein can form filaments in vitro (Necula, et al. (2003) *J. Biol. Chem.* 278:46674-80). Familial Parkinson's disease due to mutations in α-synuclein exhibit a rapid progression typically with strong LB/LN pathology. In contrast, familial Parkinson's disease associated with mutations in parkin (PARK2) exhibit autosomal recessive genetics, early onset and slow progression with minimal LB pathology. Parkin is an E3 ligase and plays a role in the ubiquitin/proteasome pathway for degradation of cellular proteins (Tanaka, et al. (2004) *Biochim. Biophys. Acta* 1695: 235-47; Kitada, et al. (1998) *Nature* 392:605-8). However, there is little or no LB/LN pathology observed in familial Parkinson's disease associated with parkin (Cookson (2005) supra). As with α-synuclein, parkin is widely expressed in neurons, but nigral dopaminergic neurons appear particularly vulnerable. Mutations in DJ-1 (PARK7) and PINK1 (PARK6) also produce autosomal recessive, early onset forms of familial Parkinson's disease (Cookson (2005) supra). DJ-1 exists in both mitochondrial and cytoplasmic forms and has been implicated in protection from oxidative damage or through an antiapoptotic action (Cookson (2005) supra). PINK1 is also implicated in mitochondrial function (Cookson (2005) supra; Beilina, et al. (2005) *Proc. Natl.*

Acad. Sci. USA 102:5703-8) and has a ser/thr kinase domain of unknown specificity. PINK1 has been connected to the ubiquitination pathway and Ras/MAPK signaling (Shen (2004) Neuron 44:575-7). Furthermore, LRRK2/dardarin has been identified as PARK8 with somewhat early onset and variable LB pathology. The function of LRRK2 is unclear, although it has homology to MAPKKK kinases and Ras GTPases (Shen (2004) supra). The diversity of these Parkinson's disease genes and lack of a clear relationship among them has made it challenging to identify a pathogenic pathway and it may be that multiple pathways exist with a common endpoint, i.e., loss of nigral dopaminergic neurons.

SUMMARY OF THE INVENTION

The present invention is a method for restoring fast axonal transport in a cell which expresses a pathological synuclein protein. The method involves contacting the cell with an effective amount of an agent that inhibits Protein Kinase C mu or Src-Family Non-receptor Tyrosine Kinase activity thereby restoring fast axonal transport in the cell.

The present invention also embraces a method for treating a synucleinopathy by administering to a subject with a synucleinopathy an effective amount of a Protein Kinase C mu or Non-receptor Tyrosine Kinase activity (i.e., src family) inhibitor. In particular embodiments, the synucleinopathy is Parkinson's disease.

BRIEF DESCRIPTION OF THE DRAWINGS

FIG. 2 shows that mutant forms of α-synuclein associated with Familial Parkinson's disease affect the balance between AT and RT, whereas wild-type soluble forms do not. As compared to wild-type α-synuclein (FIG. 2A), both Ala30Pro (FIG. 2B) and Ala53Thr (FIG. 2C) forms of α-synuclein increase RT and decrease AT.

DETAILED DESCRIPTION OF THE INVENTION

Figure 1A:
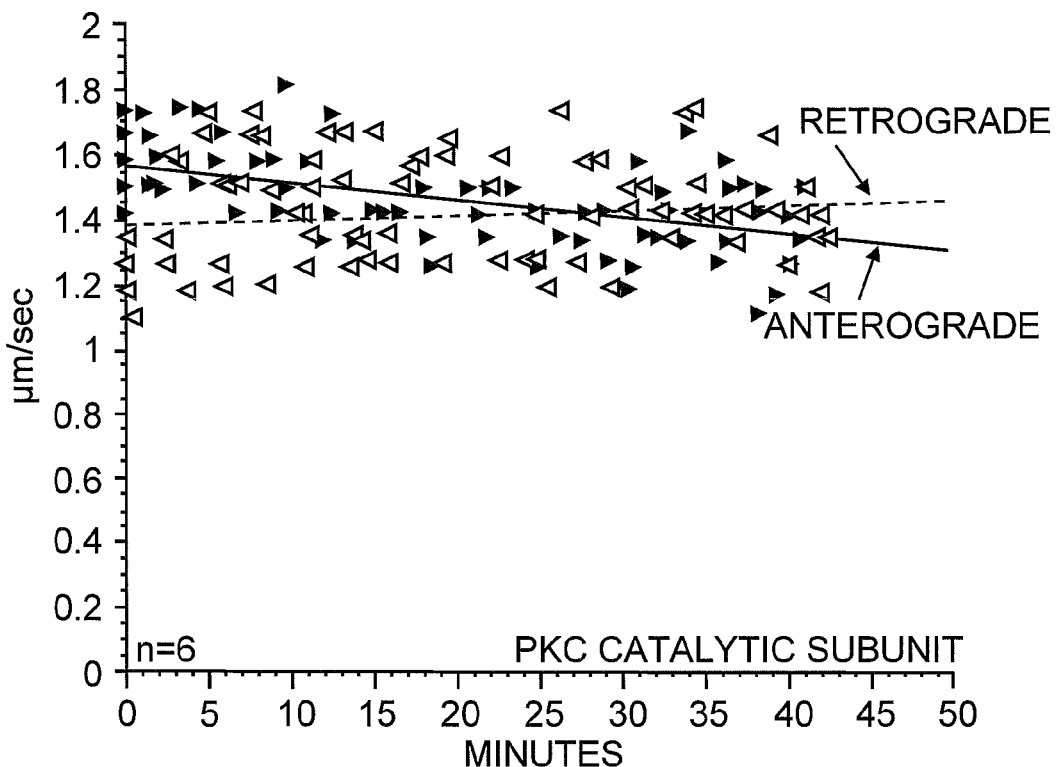
FIG. 1 shows the effects of PKC serine/threonine kinases and Fyn tyrosine kinase on fast axonal transport. Both conventional (FIG. 1A) and novel PKCs (FIG. 1B) affect fast axonal transport similarly: increasing retrograde transport (RT) and reducing anterograde transport (AT). The action of the nonreceptor tyrosine kinase Fyn (FIG. 1C) on fast axonal transport was indistinguishable from the effects of PKCs, wherein Fyn effects were blocked by 100 nM Gö6976 (FIG. 1D), which inhibits all PKCs at the concentration employed. Src has a similar effect on axonal transport and is also inhibited by Gö6976. The effect of Gö6976 in blocking Fyn and Src effects on fast axonal transport indicates that Fyn and Src effects are mediated by downstream signaling through one or more PKC.

It has now been shown that mutant forms of α-synuclein associated with familial Parkinson's disease affect the balance between anterograde transport and retrograde transport by increasing the amount and average rate of dynein-based retrograde axonal transport, while inhibiting kinesin-based anterograde axonal transport. Wild-type synuclein assembled into Lewy filaments have the same effects on axonal transport as the mutant synucleins. Introduction of these pathological forms of synuclein into the presynaptic terminal also results in a failure of neurotransmission. Specific biochemical and pharmacological inhibitors were used to define key components of the signaling pathway that lead to these changes in axonal transport and failure of neurotransmission. For pathological synuclein, these components are protein kinase C mu (PKCmu) and a Src-Family Tyrosine Kinase. As such, these kinases serve as therapeutic targets to limit, delay or prevent the loss of dopaminergic neuron function in synucleinopathies.

Accordingly, the present invention is a method for restoring fast axonal transport defects in a cell which expresses a pathological synuclein protein by inhibiting Protein Kinase C mu or Src-Family Tyrosine Kinase activity. For the purposes of the present invention, fast axonal transport is defined as kinesin- and dynein-mediated movement of mitochondria, lipids, synaptic vesicles, proteins, and other membrane-bound organelles and cellular components to and from a neuron's cell body through the axonal cytoplasm (the axoplasm) (Morfini, et al. (2006) In: Basic Neurochemistry (Ed. Siegel, et al.) pp. 485-502). Axonal transport is also responsible for moving molecules destined for degradation from the axon to lysosomes to be broken down. Axonal transport can be divided into anterograde and retrograde categories. Anterograde transport carries products like membrane-bound organelles, cytoskeletal elements and soluble substances away from the cell body towards the synapse and other axonal subdomains (Morfini, et al. (2006) In: Basic Neurochemistry (Siegel et al., ed.) Boston, Mass.: Elsevier Academic Press, pp. 485-502; Hirokawa & Takemura (2005) *Nat. Rev. Neurosci.* 6:201-14). Retrograde transport sends chemical messages and endocytosis products headed to endolysosomes from the axon back to the cell. In accordance with the disclosure provided herein, agents that inhibit Protein Kinase C mu or Non-receptor Src-Family Tyrosine Kinase activity can prevent the abnormal increase in the amount and average rate of dynein-based retrograde axonal transport, or the associated decrease in kinesin-based anterograde axonal transport in cells expressing pathological synuclein.

Cells which express a pathological synuclein protein include cells, in particular neurons, from a subject with a synucleinopathy as well as neurons from a model system (e.g., an animal model or neuronal cell line as disclosed herein) of a synucleinopathy. In this regard, by endogenously or exogenously expressing the pathological synuclein protein, the cells undergo pathogenesis. Recombinant expression of exogenous proteins in cells is conventional in the art and any suitable method can be employed. In some embodiments, cells of the present invention are isolated (e.g., grown in vitro). In other embodiments, cells of the instant method are in vivo.

A pathological synuclein protein is defined as a mutant synuclein protein, which is associated with familial Parkinson's disease, as well as a wild-type synuclein, which assembles into Lewy filaments, wherein expression of these pathological forms of synuclein in the presynaptic terminal results in a failure of neurotransmission and alteration of fast axonal transport. Pathological α-synuclein is the primary fibrillar component of Lewy bodies, and α-synuclein lesions are also observed in cases of dementia with Lewy bodies and multiple system atrophy, the parkinsonism-dementia complex of Guam, and Hallervorden-Spatz disease (Goedert (2001) *Nat. Rev. Neurosci.* 2:492-501). Moreover, β- and γ-synuclein proteins are both associated with hippocampal axon pathology in Parkinson's disease and dementia with Lewy bodies (Galvin, et al. (1999) *Proc. Natl. Acad. Sci. USA* 96:13450-13455). Accordingly, while some embodiments of the present invention embrace α-synuclein protein as the pathological synuclein, other embodiments embrace β-synuclein proteins or γ-synuclein proteins as the pathological synuclein.

Pathological synuclein proteins are well-known in the art and can be isolated or expressed from nucleotide sequences obtained from a variety of species. Table 1 provides a list of suitable synuclein proteins of use in accordance with the present invention.

TABLE 1

| Synuclein Protein | Alternative Name | GENBANK Accession No. |
|---|---|---|
| α-Synuclein | | |
| Human | NACP | NP_009292, NP_000336 |
| Rat | SYN1, SYN2, SYN3 | NP_062042 |
| Mouse | SYN2 | NP_033247 |
| Chicken | | AAF67728 |
| β-Synuclein | | |
| Human | | NP_003076 |
| Bovine | PNP14 | P33567 |
| Rat | PNP14 | Q63754 |
| Mouse | | NP_291088 |
| Chicken | | AAF67730 |
| γ-Synuclein | | |
| Human | BCSG1, persyn | NP_003078 |
| Bovine | Synoretin | AAF32342 |

TABLE 1-continued

| Synuclein Protein | Alternative Name | GENBANK Accession No. |
|---|---|---|
| Rat | | NP_113876 |
| Mouse | persyn | NP_035560 |
| Chicken | persyn | AAF67729 |

Mutant forms of synuclein proteins are also known in the art and include human α-synuclein point mutations Ala30Pro and Ala53Thr associated with Parkinson's disease 1, and Glu46Lys associated with Lewy body dementia; and human β-synuclein point mutations Val70Met and Pro123H is associated with Lewy body dementia (Ohtake, et al. (2004) *Neurology* 63: 805-811).

In accordance with the present invention, fast axonal transport defects are corrected, restored or preserved in a cell by inhibiting or decreasing Protein Kinase C mu (PKCmu) or Non-receptor (i.e., Src-Family) Tyrosine Kinase activity. In one embodiment of the present invention, inhibition of kinase activity is intended to mean that the inhibitor decreases the activity of an isolated kinase enzyme (e.g., >90% pure) in an in vitro kinase assay. In another embodiment of the present invention, inhibition of kinase activity is intended to mean that the inhibitor specifically decreases expression of the kinase of interest thereby inhibiting the kinase activity. For example, RNAi or antisense molecules are routinely used in the art to specifically decrease expression of a protein of interest.

An effective amount of an inhibitor of the invention is an amount that measurably decreases or inhibits any property (e.g., phosphorylation), biochemical activity (e.g., a kinase activity or an ability to bind to another protein) or biological activity possessed by the kinase of interest as compared to the kinase of interest when not contacted with the inhibitor. By inhibiting or decreasing Protein Kinase C mu (PKCmu) or Non-receptor (i.e., Src-Family) Tyrosine Kinase activity in accordance with the present invention, defects in fast axonal transport are restored or preserved.

PKCmu, also known as protein kinase D1, is a serine/threonine kinase whose activation is dependent on the phosphorylation of two activation loop sites, Ser744 and Ser748, via a PKC-dependent signaling pathway (Valverde, et al. (1994) *Proc. Natl. Acad. Sci.* 91:8572-8576; Johannes, et al. (1994) *J. Biol. Chem.* 269:6140-6148; Iglesias, et al. (1998) *J. Biol. Chem.* 273:27662-27667). Human PKD/PKCmu protein is known in the art and set forth under GENBANK Accession No. NM_002742.

PKCmu inhibitors of the present invention include chemical inhibitors, protein-based inhibitors, nucleic acid-based inhibitors, or mixtures thereof. Chemical inhibitors include small organic molecules that inhibit the activity of PKCmu. An example of a chemical inhibitor is Gö66976 (5,6,7,13-Tetrahydro-13-methyl-5-oxo-12H-indolo[2,3-a]pyrrolo[3,4-c]carbazole-12-propanenitrile), which is a broad spectrum inhibitor of PKC family kinases that also inhibits PKCmu. Moreover, resveratrol has been shown to inhibit PKD autophosphorylation ($IC_{50}$=52 μM) and PKD phosphorylation of the exogenous substrate syntide-2 ($IC_{50}$=36 μM), with only negligible effects against the autophosphorylation reactions of representative members of each PKC isozyme subfamily, i.e., cPKC-alpha, cPKC-beta, cPKC-gamma, nPKC-delta and nPKC-epsilon, and aPKC-zeta (Stewart, et al. (2000) *Biochem. Pharmacol.* 60(9):1355-9). Gö6976 is commercially available from sources such as Biomol Laboratories (Plymouth Meeting, Pa.).

Protein-based inhibitors of PKCmu include inhibitors which are composed of amino acid residues. Examples of protein-based inhibitors include peptide substrates which mimic in vivo substrates thereby diluting PKCmu activity, as well as antibodies which bind PKCmu or PKCmu substrates and block activation of PKCmu or PKCmu substrates. An exemplary protein-based inhibitor is the MARCKS peptide available AnaSpec (San Jose, Calif.).

Nucleic acid-based inhibitors include inhibitors which inhibit the transcription or translation of PKCmu mRNA. Examples of such inhibitors include RNAi or antisense molecules such as those disclosed by Zhang et al. ((2005) *J. Biol. Chem.* 280:19036-19044) and Wang, et al. ((2004) *J. Biol. Chem.* 279(51):53674-82), respectively.

Changes in PKCmu activity can be detected as disclosed herein or via phosphorylation of a biotinylated peptide substrate containing the residues surrounding serine 133 of CREB (e.g., Arg-Arg-Pro-Ser-Tyr-Arg-Lys; SEQ ID NO:1) or syntide-2 (H-Pro-Leu-Ala-Arg-Thr-Leu-Ser-Val-Ala-Gly-Leu-Pro-Gly-Lys-Lys-OH; SEQ ID NO:2), or alternatively in a high-throughput, non-radioactive enzyme-linked immunosorbent assay (ELISA) using myelin basic protein (MBP) as substrate (Rykx, et al. (2007) *Assay Drug Dev. Technol.* 5(5):637-644).

As used herein, the term "Non-receptor Tyrosine Kinase protein" or "Src-Family Tyrosine Kinase protein", refers to a protein having amino acid sequence homology to v-Src, wherein said protein has N-terminal myristolation, a conserved domain structure having an N-terminal variable region, followed by a SH3 domain, a SH2 domain, a tyrosine kinase catalytic domain and a C-terminal regulatory domain. Src-Family Tyrosine Kinase members are well-known in the art and include Src, Lck, Hck, Fyn, Blk, Lyn, Fgr, Yes, and Yrk. In particular embodiments, an inhibitor of the invention inhibits the activity of one or more of the members of the Src-Family or other non-receptor tyrosine kinases with similar biological and pharmacological specificity. In specific embodiments, the Src-Family Tyrosine Kinase is Fyn or Src.

Suitable Src-Family Tyrosine Kinase inhibitors for purposes of the present invention include chemical inhibitors such as the pyrazolopyrimidine class of Src-Family Tyrosine Kinase inhibitors, the macrocyclic dieneone class of Src-Family Tyrosine Kinase, the pyrido[2,3-d]pyrimidine class of Src-Family Tyrosine Kinase inhibitors, and the 4-anilino-3-quinoline carbonitrile class of Src-Family Tyrosine Kinase inhibitors, wherein mixtures of inhibitors can also be utilized.

Exemplary pyrazolopyrimidine class inhibitors include, 4-amino-5-(4-methylphenyl)-7-(t-butyl)pyrazolo[3,4-d-]pyrimidine (also referred to as PP1 or AGL1872), 4-amino-5-(4-chlorophenyl)-7-(t-butyl) pyrazolo[3,4-d-]pyrimidine (also referred to as PP2 or AGL1879), and the like, the detailed preparation of which are described by Waltenberger, et al. ((1999) *Circ. Res.* 85:12-22). PP1 and PP2 are commercially available from sources such as Biomol Laboratories and Calbiochem (San Diego, Calif.), respectively. See also Hanke, et al. (1996) *J. Biol. Chem.* 271(2):695-701. In particular embodiments, the inhibitor employed in accordance with the present invention is a pyrazolopyrimidine inhibitor, most desirably PP1 or PP2.

Examples of macrocyclic dienone inhibitors include Radicicol R2146, Geldanamycin, Herbimycin A, and the like. The macrocyclic dienone inhibitors are composed of a 12 to 20 carbon macrocyclic lactam or lactone ring structure containing an α, β, γ, 6-bis-unsaturated ketone (i.e., a dienone) moiety and an oxygenated aryl moiety as a portion of the macrocyclic ring. These inhibitors are known in the art and commercially available from sources such as Calbiochem and Sigma (St. Louis, Mo.).

The pyrido[2,3-d]pyrimidine class of inhibitors include, for example PD173955 and the like. The structure of PD173955 is provided by Moasser, et al. ((1999) *Cancer Res.* 59:6145-6152) and is commercially available from Parke-Davis Pharmaceuticals (Ann Arbor, Mich.).

An exemplary 4-anilino-3-quinoline carbonitrile class inhibitor is SKI-606, available from Wyeth (Madison, N.J.).

Other specific Src kinase inhibitors useful in the methods and compositions of the present invention include PD 162531 (Owens, et al. (2000) *Mol. Biol. Cell* 11:51-64) available from Parke-Davis Pharmaceuticals as well as peptide-based inhibitors of Src kinases.

Additional suitable kinase inhibitors can be identified and characterized using standard assays known in the art. For example, screening of chemical compounds for potent and selective inhibitors for Src or other tyrosine kinases has been done and has resulted in the identification of chemical moieties useful in potent inhibitors of Src-Family Tyrosine Kinases. For example, U.S. Patent Application No. 20040176313 discloses a method for screening for a therapeutic compound in the treatment of Alzheimer's disease by identifying a Src protein inhibitor.

By way of illustration, catechols have been identified as important binding elements for a number of tyrosine kinase inhibitors derived from natural products, and have been found in compounds selected by combinatorial target-guided selection for selective inhibitors of c-Src. See Maly, et al. (2000) *Proc. Natl. Acad. Sci. USA* 97(6):2419-2424. Combinatorial chemistry-based screening of candidate inhibitor compounds, using moieties known to be important to PKCmu or Src inhibition as a starting point, is a potent and effective means for isolating and characterizing other chemical inhibitors of PKCmu or Src-Family Tyrosine Kinases.

Restoration of fast axonal transport in a cell finds application in research focusing on mechanisms of fast axonal transport and pathological synuclein activity as well as in the amelioration, delay, or prevention of synucleinopathies. As is conventional in the art, the term synucleinopathy is used to name a group of neurodegenerative disorders associated with pathological synuclein protein, particularly α-synuclein, in the cytoplasm of selective populations of neurons and glia, and in particular in which the presence of synuclein-containing inclusions are pathognomic for the disease. This should be distinguished from non-synucleinopathy disorders in which synuclein-containing inclusions may or may not be present in addition to other pathologies. For example, while synuclein-containing inclusions have been found in Alzheimer's patients, Alzheimer's disease is characterized by a build-up of ADDLs, and deposits of beta-amyloid and tau that respectively accumulate in the spaces between nerve cells and inside nerve cells. Synucleinopathies particularly embraced by the present invention include Parkinson's disease, dementia with Lewy bodies (DLB), multiple system atrophy (MSA), toxin-induced Parkinson's disease, pure autonomic failure (PAF) and Hallervorden-Spatz disease. In particular embodiments, the synucleinopathy is Parkinson's disease. In specific embodiments the synucleinopathy is sporadic and familial Parkinson's disease.

Treatment in accordance with the present invention includes administering, to a subject with a synucleinopathy, an effective amount of a Protein Kinase C mu or Src-Family Tyrosine Kinase inhibitor so that one or more signs or symptoms of the disease are ameliorated, delayed or prevented. In this regard, it is not necessary that the pathological synuclein be altered or degraded. In particular embodiments, treatment results in the restoration of fast axonal transport and dopaminergic neuron function as compared to a subject not receiving such treatment.

Subjects benefiting from such treatment include humans as well as other animals which develop synucleinopathies. In this context, a subject is understood to include any mammalian species in which treatment of a synucleinopathy is desirable, including agricultural and domestic mammalian species, as well as humans. The dosage ranges for the administration of the inhibitors of the invention can be in the range of about 0.1 mg/kg body weight to about 100 mg/kg body weight, or the limit of solubility of the active compound in a pharmaceutically acceptable carrier.

Kinase inhibitors, as described herein, can be used to prepare medicaments for treatment of a synucleinopathy. The inhibitors can be included in pharmaceutical compositions useful for practicing the therapeutic method described herein. Pharmaceutical compositions of the present invention contain a physiologically acceptable carrier together with a kinase inhibitor as described herein, dissolved or dispersed therein as an active ingredient. In a particular embodiment, the pharmaceutical composition is not immunogenic when administered to a mammalian patient, such as a human, for therapeutic purposes.

Kinase inhibitors of the present invention can be administered subcutaneously, intravenously, parenterally, intraperitoneally, intradermally, intramuscularly, topically, enteral (for example, orally), rectally, nasally, buccally, vaginally, by inhalation spray, by drug pump or via an implanted reservoir in dosage formulations containing conventional non-toxic, physiologically (or pharmaceutically) acceptable carriers or vehicles.

In a specific embodiment, it may be desirable to administer the inhibitor of the invention locally to a localized area in need of treatment; this can be achieved by, for example, and not by way of limitation, local infusion during surgery, topical application, transdermal patches, by injection, by means of a catheter, by means of a suppository, or by means of an implant, said implant being of a porous, non-porous, or gelatinous material, including membranes, such as silastic membranes or fibers. When it is desirable to direct the inhibitor to the central nervous system, techniques which can opportunistically open the blood brain barrier for a time adequate to deliver the drug there through can be used. For example, a composition of 5% mannitose and water can be used.

Suitable pharmaceutically acceptable carriers include but are not limited to water, salt solutions (for example, NaCl), alcohols, gum arabic, vegetable oils, benzyl alcohols, polyethylene glycols, glycerol, gelatin, carbohydrates such as lactose, amylose or starch, magnesium stearate, talc, silicic acid, viscous paraffin, perfume oil, fatty acid esters, hydroxymethylcellulose, polyvinyl pyrolidone, and combinations thereof. The pharmaceutical preparations can be sterilized and if desired, mixed with auxiliary agents, for example, lubricants, preservatives, stabilizers, wetting agents, emulsifiers, salts for influencing osmotic pressure, buffers, coloring, flavoring and/or aromatic substances and the like which do not deleteriously react with the active agents.

The compositions, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The compositions can be formulated in accordance with the routine procedure as a pharmaceutical composition adapted for intravenous administration to human beings. Typically, compositions for intravenous administration are solutions in sterile isotonic aqueous buffer. Where necessary, the composition can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water, saline or dextrose/water. Where the composition is administered by injection, an ampoule of sterile water for injection or saline can be provided so that the ingredients may be mixed prior to administration.

For topical application, there are employed as nonsprayable forms, viscous to semi-solid or solid forms including a carrier compatible with topical application and having a dynamic viscosity preferably greater than water. Suitable formulations include, but are not limited to, solutions, suspensions, emulsions, creams, ointments, powders, enemas, lotions, sols, liniments, salves, aerosols, etc., which are, if desired, sterilized or mixed with auxiliary agents, for example, preservatives, stabilizers, wetting agents, buffers or salts for influencing osmotic pressure, etc. The drug may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

The amount of inhibitor which will be effective in the treatment of a particular synucleinopathy may be dependent upon the synucleinopathy, age of the subject, health status of the subject and the like, and can be determined by standard clinical techniques. In addition, in vitro or in vivo assays can optionally be employed to help identify optimal dosage ranges. The precise dose to be employed in the formulation will also depend on the route of administration, and the seriousness of the disease or disorder, and should be decided according to the judgment of the practitioner and each patient's circumstances.

The invention is described in greater detail by the following non-limiting examples.

Example 1

Materials and Methods

Antibodies and Reagents.

All reagents were from Sigma unless otherwise specified. The following antibodies were used: H2 and 63-90 mAb anti-KHC (Stenoien & Brady (1997) *Mol. Biol. Cell.* 8(4): 675-89); 74.1 monoclonal antibody against DIC (Chemicon); tubulin antibody (Clone DM1a, Sigma). PKCmu and PKCdelta peptide substrates, Gö6976, Gö6983, and Caspase-3 Inhibitor II were obtained from Calbiochem. PP2 tyrosine kinase inhibitor was from Alexis Biochemicals. Enzymes (PKCμ, Fyn, Caspase 3, etc.) were from Millipore.

Lysate Preparation/Immunoblot Analysis.

Cell cultures were homogenized in ROLB buffer (10 mM HEPES pH 7.4, 0.5% TRITON X-100, 80 mM β-glycerophosphate, 50 mM Sodium Fluoride, 2 mM Sodium Orthovanadate, 100 nM Staurosporine, 100 nM K252a, 50 nM Okadaic acid, 50 nM Microcystin, 100 mM Potassium Phosphate and mammalian protease inhibitor cocktail (Sigma)). Lysates were clarified by centrifugation and protein concentration determined using BCA kit (Pierce). Proteins were separated by SDS-PAGE and immunoblotted as described previously (Morfini, et al. (2004) *EMBO J.* 23(11):2235-45).

Motility Studies in Isolated Axoplasm.

Axoplasm was extruded from giant axons of the squid *Loligo pealeii* (Marine Biological Laboratory) according to established methods (Brady, et al. (1985) *Cell Motil.* 5(2):81-101). Axons were 400-600 μm in diameter and provided ≈5 μl of axoplasm per axon. Wild-type α-synuclein or α-synuclein with point mutations associated with familial Parkinson's disease (Ala30Pro or Ala53Thr), MPP+, enzymes or inhibitors were diluted into X/2 buffer (175 mM potassium aspartate, 65 mM taurine, 35 mM betaine, 25 mM glycine, 10 mM HEPES, 6.5 mM $MgCl_2$, 5 mM EGTA, 1.5 mM $CaCl_2$, 0.5 mM glucose, pH 7.2) supplemented with 2-5 mM ATP and 20 μl of this mix was added to perfusion chambers (Brady, et al. (1985) supra). Preparations were analyzed on a ZEISS AXIOMAT with a 100×, 1.3 na objective, and DIC optics. Hamamatsu Argus 20 and Model 2400 CCD camera were used for image processing and analysis. Organelle velocities were measured with a Photonics Microscopy C2117 video manipulator (Hamamatsu).

Phosphorylation Studies in Squid Axoplasm.

In the analysis disclosed herein, 3-4 axoplasms were triturated in KB buffer (10 mM HEPES, pH 7.4, 10 mM $MgCl_2$, 1 mM DTT) and aliquoted. Individual reactions with corresponding in vitro translated AR constructs were started by adding radiolabeled ATP to 100 μM. Reactions were performed in 50 μl, incubated for 20 minutes at room temperature and stopped with 50 μl of 2× sample buffer. Lysates were separated by SDS-PAGE and analyzed by autoradiography.

Metabolic Labeling Experiments in Cells and Squid Axoplasm.

One mCi $^{32}$P phosphate (ICN) was added per dish and incubated for 4 hours. Medium was discarded, cells homogenized in 1 ml of ROLB buffer and processed accordingly to standard methods (Morfini, et al. (2004) supra). Axoplasms were prepared as for video microscopy, but 1 mCi of $\gamma$-$^{32}$P-ATP was added. After 50 minutes incubation, axoplasms were homogenized in ROLB buffer. A 10 μl aliquot of lysate was precipitated with 15% TCA and radioactivity incorporated into protein determined by scintillation counting. Aliquots of equal counts were used for kinesin immunoprecipitation with 10 μg of 74.1 antibody and Protein G-agarose beads (Pierce). Immunoprecipitates were separated by SDS-PAGE, dried and exposed in a PHOSPHORIMAGER cassette, then scanned and quantified on a TYPHOON (Amersham/Molecular Dynamics).

Expression of α-Synucleins and Assembly of LB Filaments.

Plasmids containing wild-type α-synuclein; Ala30Pro α-synuclein and Ala53Thr α-synuclein for conventional expression in bacteria were used to generate synuclein protein used in axoplasm and squid giant synapse preparations. Protocols for generation of LB filament were a modification of known methods (Necula, et al. (2003) *J. Biol. Chem.* 278 (47):46674-80). Briefly, 8 μM recombinant α-synuclein and 75 μM arachidonic acid (Cayman Chemical) were incubated in assembly buffer (10 mM HEPES, pH 7.4, 100 mM KCl, 5 mM DTT) at 37° C. for 4 hours. Filament formation was verified by electron microscopy. Filaments were stable at room temperature for several days and could be stored for longer periods by freezing in liquid $N_2$. Assembly buffer was compatible with axoplasm studies after 1:1 dilution in buffer X. LB filaments assembled from wild-type α-synuclein were used for pharmacological and biochemical analysis of pathways for activation of room temperature. The ability of LB filaments to affect retrograde axonal transport in isolated axoplasm was evaluated, as were the effects of wild-type LB filaments on kinases.

Immunoprecipitation Kinase Assays.

Immunoprecipitation kinase assays were performed according to known methods using 500 μg of total protein from cells (Beffert, et al. (2002) *J. Biol. Chem.* 277(51): 49958-64) Control immunoprecipitates were performed with 2 μg of each normal mouse or rabbit IgG. GST-cjun or GST-MARCKS (1-89) (3 μg) was used as substrate. Reactions were carried out for 20 minutes at 30° C., in the presence of 100 μM radiolabeled $\gamma$-$^{32}$P-ATP. Samples were analyzed by SDS-PAGE and gels were dried after staining with COOMASSIE Blue. Kinase activity values were obtained using a TYPHOON PHOSPHORIMAGER after overnight exposure. Background kinase activity values from immunoprecipitates with non-immune control antibodies were subtracted.

Immunocytochemistry.

Immunocytochemical staining was performed as described (Szebenyi, et al. (2003)*Neuron* 40(1):41-52; Morfini, et al. (2002) supra). Briefly, cells were fixed for 15 minutes at 37° C. in 2% paraformaldehyde/0.01% glutaraldehyde/0.12 M sucrose in PHEM, washed in phosphate-buffered saline (PBS) and permeabilized with 0.2% TRITON X-100 in PBS for 10 minutes. Cultures were blocked for 1 hour in 2.5% gelatin/1% BSA in PBS and incubated overnight at 4° C. in a humid chamber with DM1a or N-20 primary antibodies followed by incubation with appropriate secondary antibodies conjugated with ALEXA Fluoro-red or Fluoro-green (Molecular Probes, Eugene, Oreg.). Fluorescence was visualized on a ZEISS LSM 510 Meta confocal microscope or AXIOVERT 200M inverted microscope with Openlab image processing software. Primary antibodies were used at 0.5-5 μg/ml.

Statistical Analysis.

All experiments were repeated at least three times. Unless otherwise stated, the data was analyzed by two sample t-test using Datadesk software. Data was expressed as mean±SEM and significance was assessed at p<0.05 or 0.01 as noted.

Example 2

Modulation of Fast Axonal Transport by Protein Kinase C

Figure 1B:
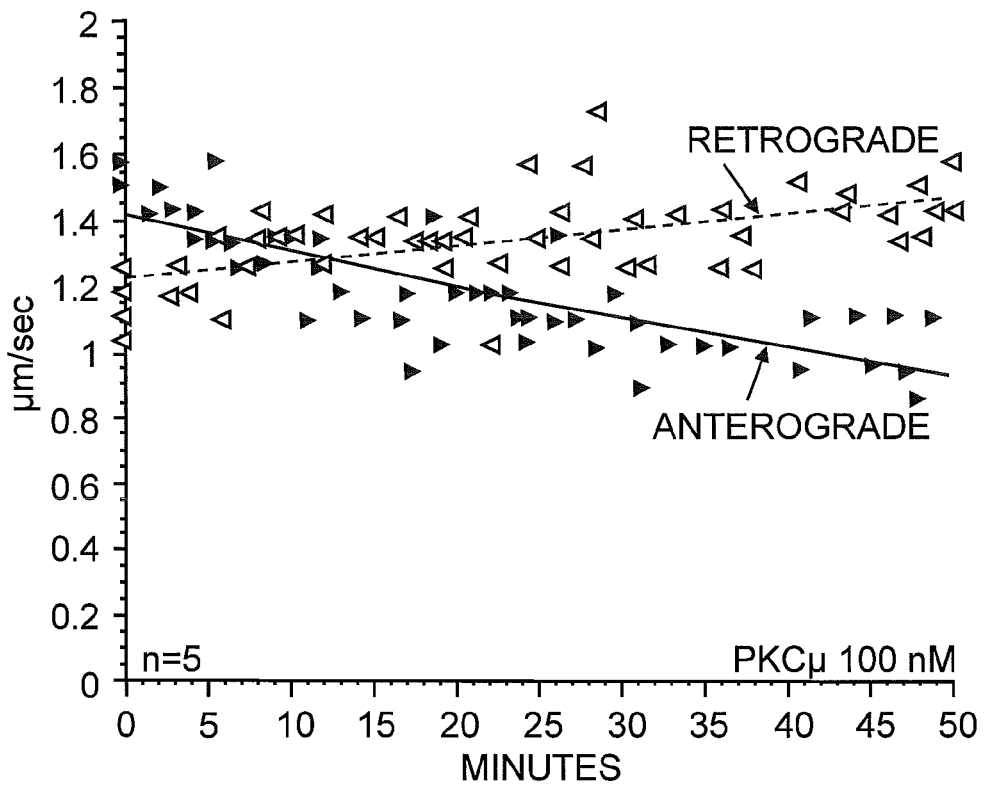

Protein kinase C enzymes play roles in many cellular activities (Parker & Murray-Rust (2004) *J. Cell Sci.* 117:131-2). During a screen of candidate kinases for regulators of fast axonal transport, a constitutively active catalytic domain of PKC (Calbiochem), generated by tryptic digest of a mix of PKCα,β,γ, was identified (FIG. 1A). Similar effects were seen after perfusion of other isoforms of PKC, e.g., PKCμ (FIG. 1B), which has been variably termed a novel PKC (Liu & Heckman (1998) *Cell Signal* 10:529-42), a PKC-related kinase (Guo, et al. (2004) *Curr. Opin. Immunol.* 16:367-73; Rykx, et al. (2003) *FEBS Lett.* 546:81-6) and the novel PKCδ (Kikkawa, et al. (2002) *J. Biochem.* (Tokyo) 132:831-9). PKCs have a distinctive effect on fast axonal transport: a rapid increase in the amount and rate of retrograde fast axonal transport accompanied by a slow decline in anterograde fast axonal transport. The effects of PKC on retrograde transport correlated with increased phosphorylation of dynein intermediate chain and indicated that one or more PKCs play a role in the turnaround of membrane-bounded organelles in transport (Morfini, et al. (2007) supra)

Example 3

Modulation of Fast Axonal Transport by Nonreceptor Tyrosine Kinases

Figure 1C:
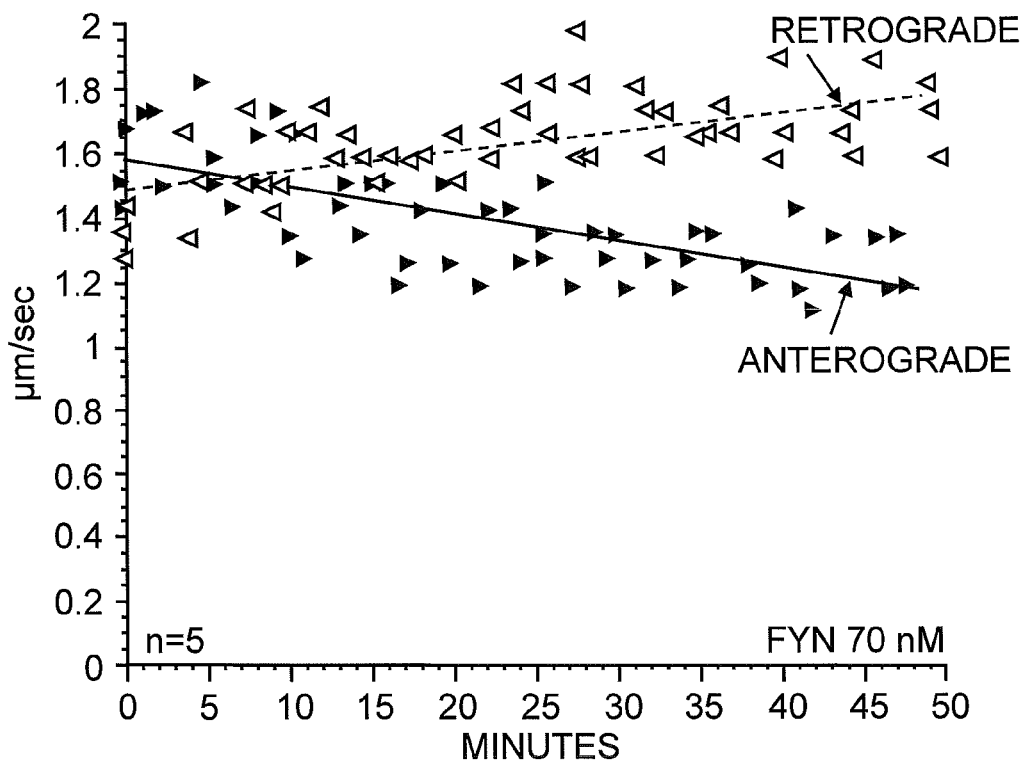
Figure 1D:
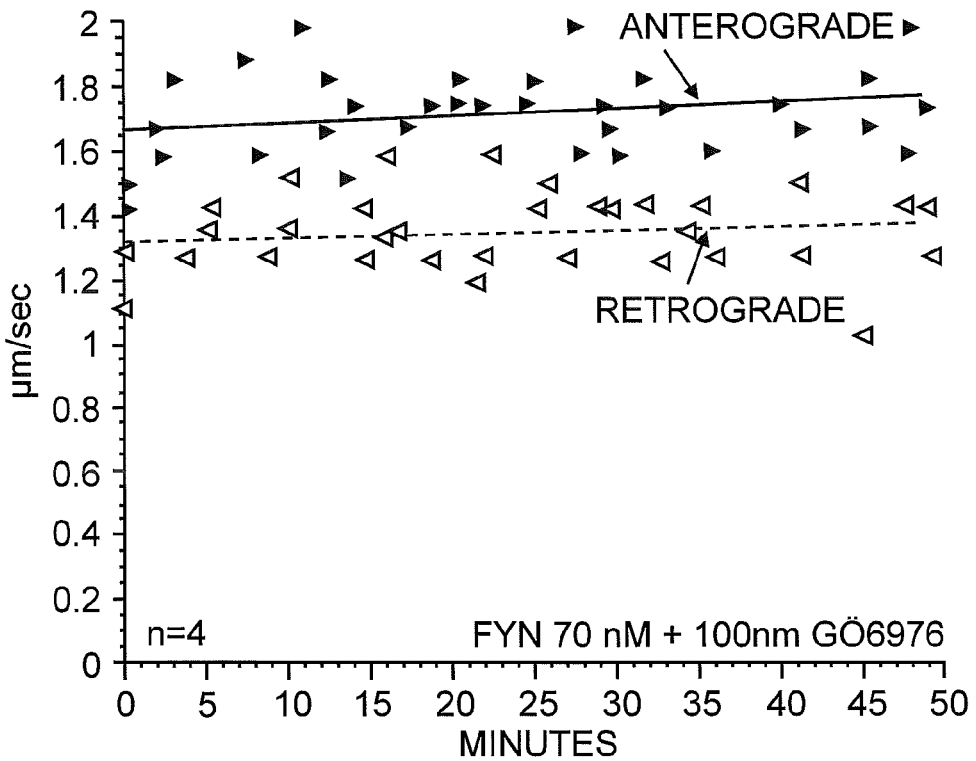

Studies on signaling by the reelin receptor (Beffert, et al. (2004) *J. Neurosci.* 24:1897-906; Beffert, et al. (2002) *J. Biol. Chem.* 277:49958-49964) suggested that nonreceptor tyrosine kinases might also affect fast axonal transport. Screening of nonreceptor tyrosine kinases included Src- and Abl-family members. Abl-family members had no effect on transport, but Src and Fyn had a striking effect on fast axonal transport (FIG. 1C), producing a rapid increase in the amount and rate of retrograde transport accompanied by a slow decline in anterograde transport similar to the effects of PKCs. Given that neither kinesin nor dynein are known to have tyrosine phosphorylations, the ability of a broad spectrum PKC inhibitor Gö6976 was included in the assay to block the action of Fyn. Gö6976 inhibition of PKC abolished actions of Src/Fyn on fast axonal transport (FIG. 1D), as did perfusion of the MARCKS peptide. In contrast, the closely related compound Gö6983, which is also effective at inhibiting conventional PKCs, and some, but not all, novel PKCs did not block the action of Src/Fyn. This differential effect indicated that novel PKCs were downstream of Src/Fyn.

Concurrent studies showed that certain receptor tyrosine kinases could also mediate regulation of retrograde transport, an effect that was blocked by the broad spectrum PKC inhibitor Gö6976. Specifically, NGF and BDNF binding to Trk neurotrophin receptors caused a shift in the apparent molecular weight of dynein intermediate chain (DIC). To identify the kinase pathway involved in this change, more than 30 different kinase and phosphatase inhibitors were screened. The results of this analysis indicated that only the broad-spectrum PKC inhibitor Gö6976 at 100 nM was able to block the effect. The closely related compound Gö6983, which inhibits conventional atypical PKCs, failed to block phosphorylation of DIC.

The shift in DIC immunoreactivity occurred within 5 minutes of treatment with BDNF and could be reversed by treatment of samples with alkaline phosphatase, indicating that the shift was due to phosphorylation of DIC. Stimulation of Reelin receptors, which also activate a Src-Family Tyrosine Kinase (Gatti (2004) *Cell Mol. Neurobiol.* 24:461-75) produced a similar increase in DIC phosphorylation, an effect which was also blocked by Gö66976.

Example 4

Modulation of Fast Axonal Transport in Familial Parkinson's Disease

Figure 2A:
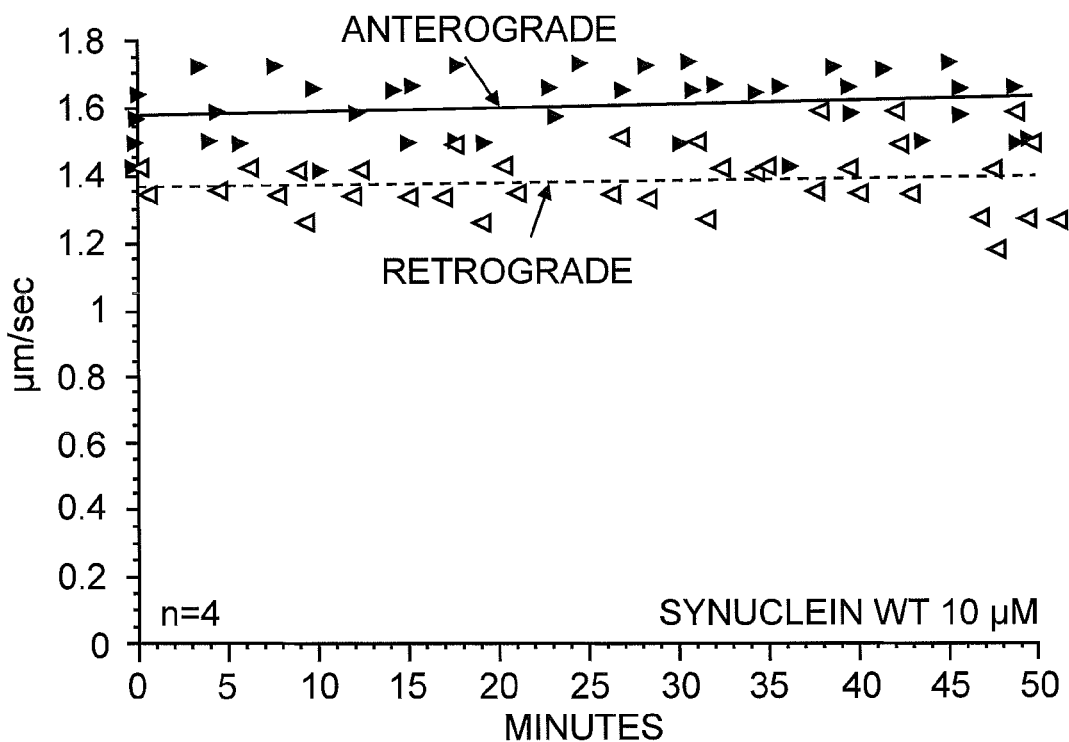
Figure 2B:
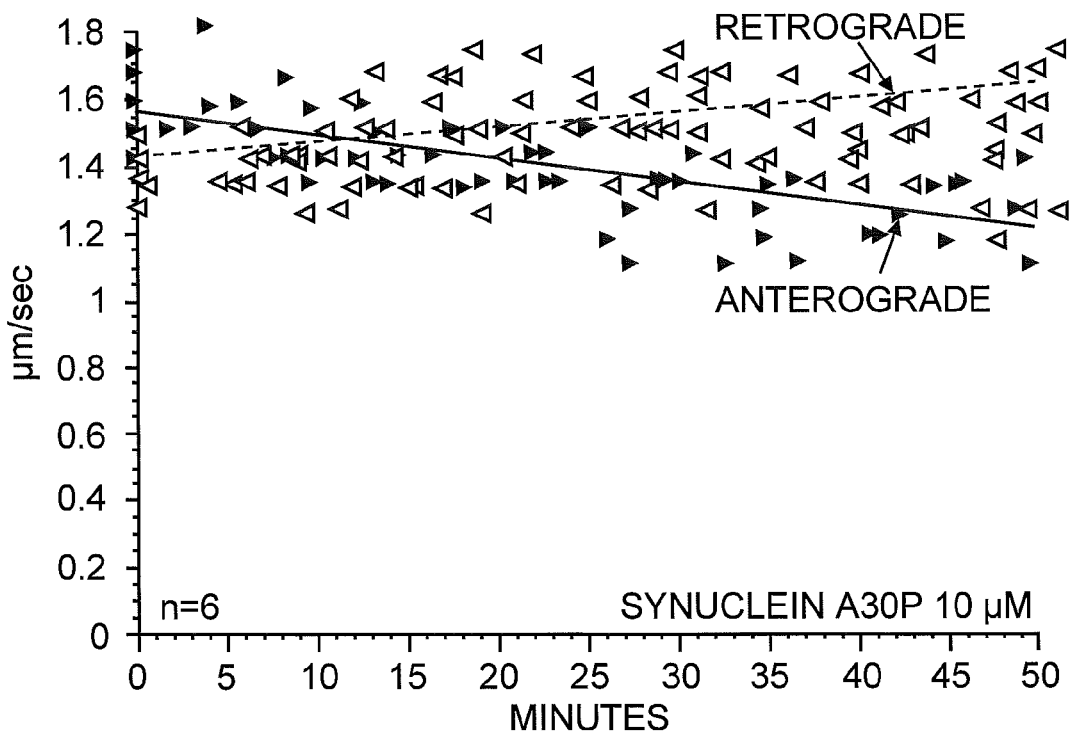
Figure 2C:
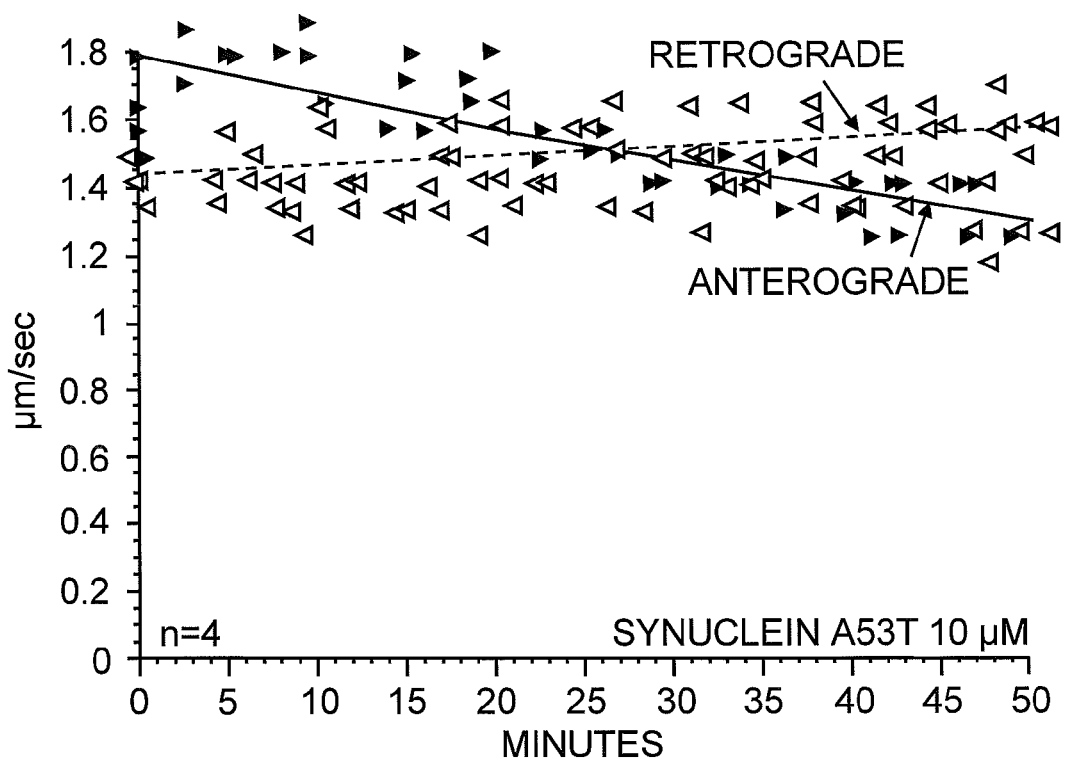

In Parkinson's disease, dopaminergic neurons are affected in the substantia nigra with initial loss of synaptic function followed by eventual neuronal death. A distinctive pathological hallmark is the presence of LB and LN aggregates formed from α-synuclein. Using the mutant α-synucleins associated with familial Parkinson's disease, changes in fast axonal transport in familial Parkinson's disease were evaluated (FIG. 2). Introduction of either Ala30Pro (FIG. 2B) or Ala53Thr (FIG. 2C) mutant α-synuclein produced an identical effect on retrograde transport and anterograde transport, namely dynein-based retrograde transport was rapidly increased and kinesin-based anterograde transport gradually declined in the presence of mutant α-synucleins. These effects were comparable to those seen with treatment of axoplasm with either PKC catalytic subunit or Src-Family Nonreceptor Tyrosine Kinase Fyn.

Figure 3A:
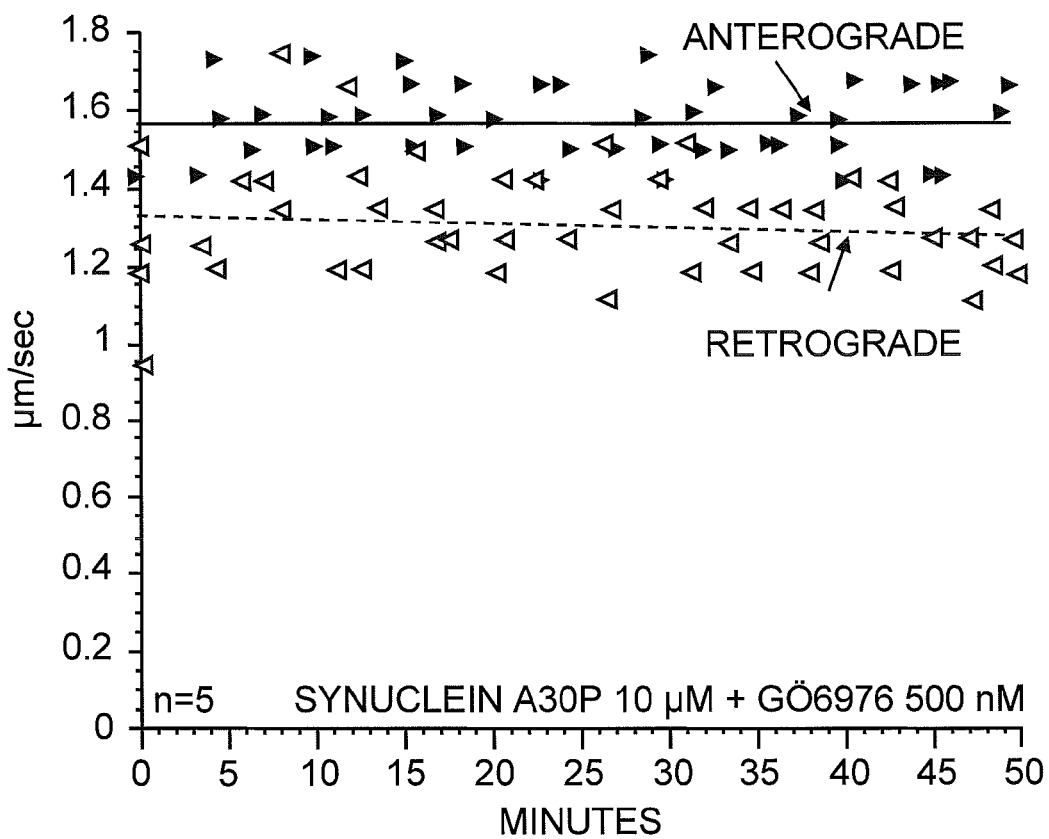
FIG. 3 shows the activity of inhibitors of PKCmu (Gö6976, FIG. 3A; and PKCmu peptide substrate, FIG. 3B), Src family tyrosine kinases (PP2, FIG. 3C), Caspase 3 (Caspase 3 inhibitor, FIG. 3D), and PKCdelta (PKCdelta peptide substrate, FIG. 3E; and Gö6983, FIG. 3F) in blocking the effect of familial Parkinson's disease mutant α-synuclein. Only inhibitors active against PKCmu or Src family tyrosine kinases (Gö6976, PKCmu peptide substrate, and PP2) are effective at blocking the actions of familial Parkinson's disease mutant α-synuclein on fast axonal transport. Inhibitors directed against other pathways (Caspase inhibitor) or other PKC isoforms (Gö6983, PKCdelta peptide substrate) are ineffective.
Figure 3B:
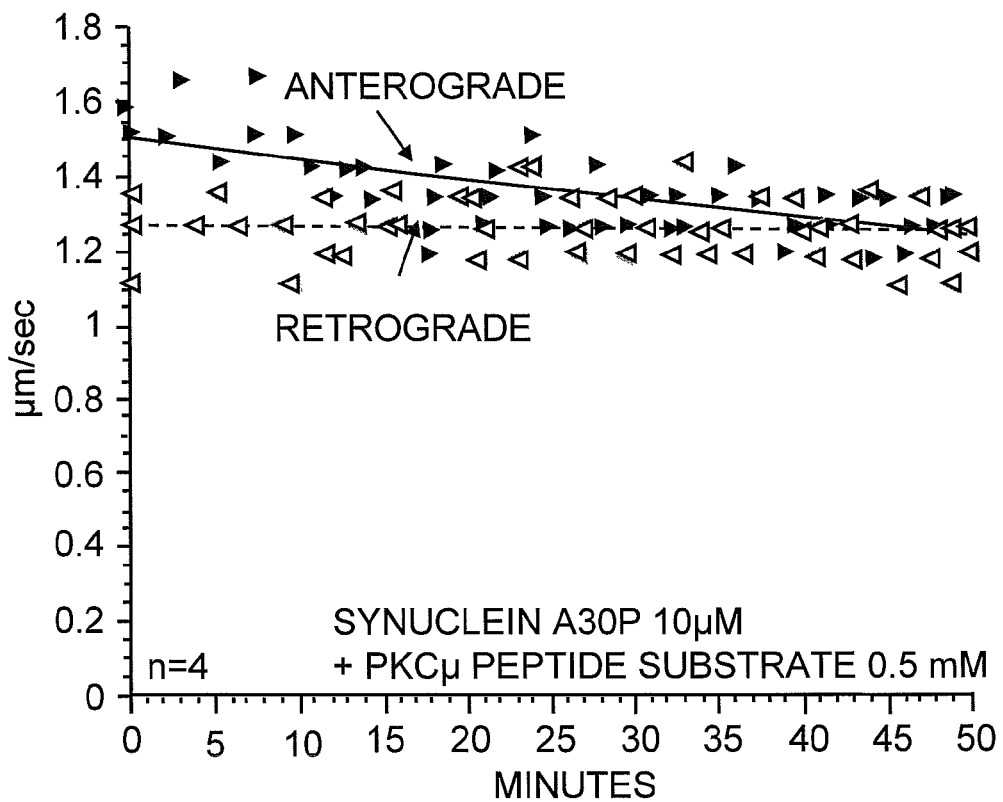
Figure 3C:
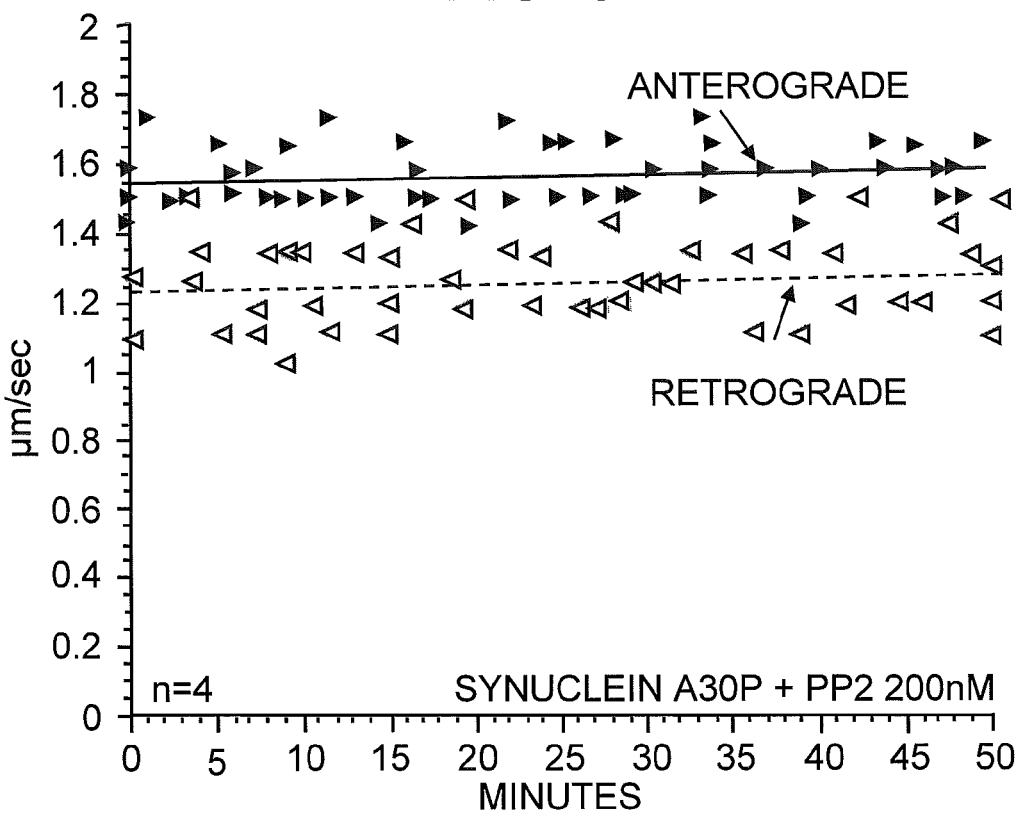
Figure 3D:
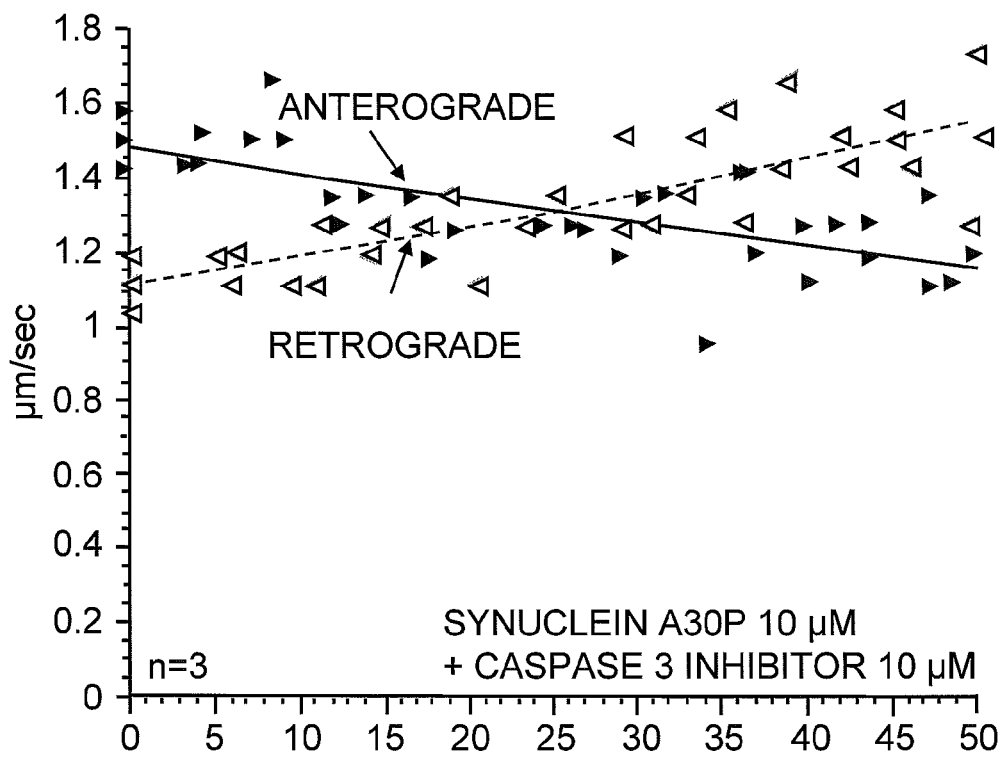
Figure 3E:
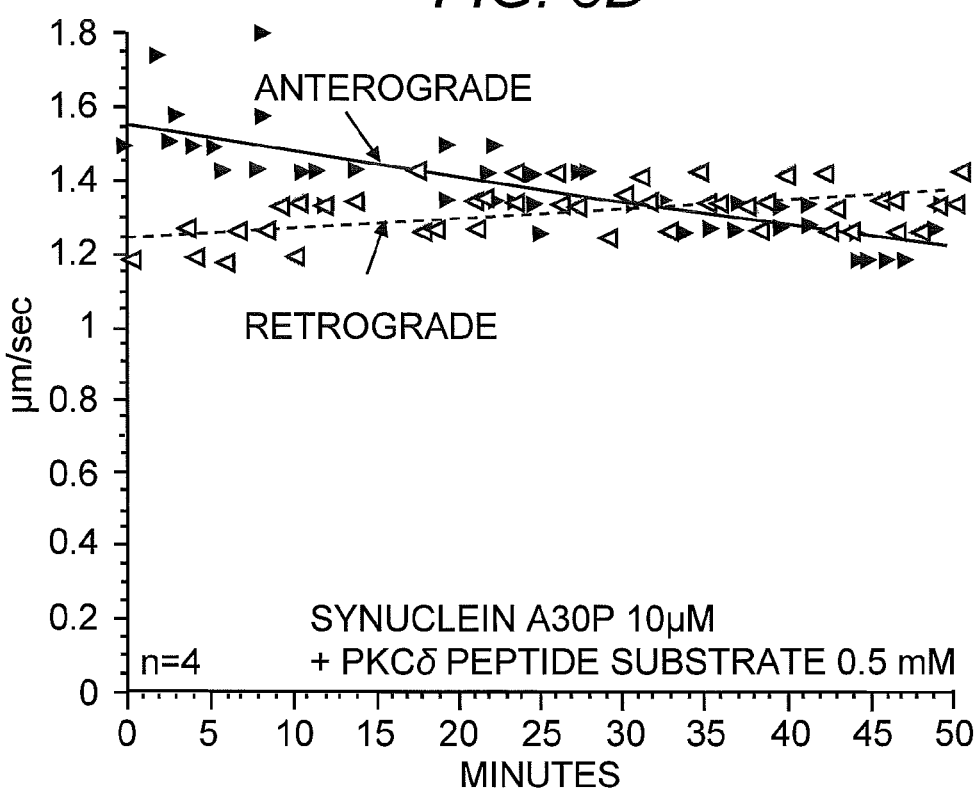
Figure 3F:
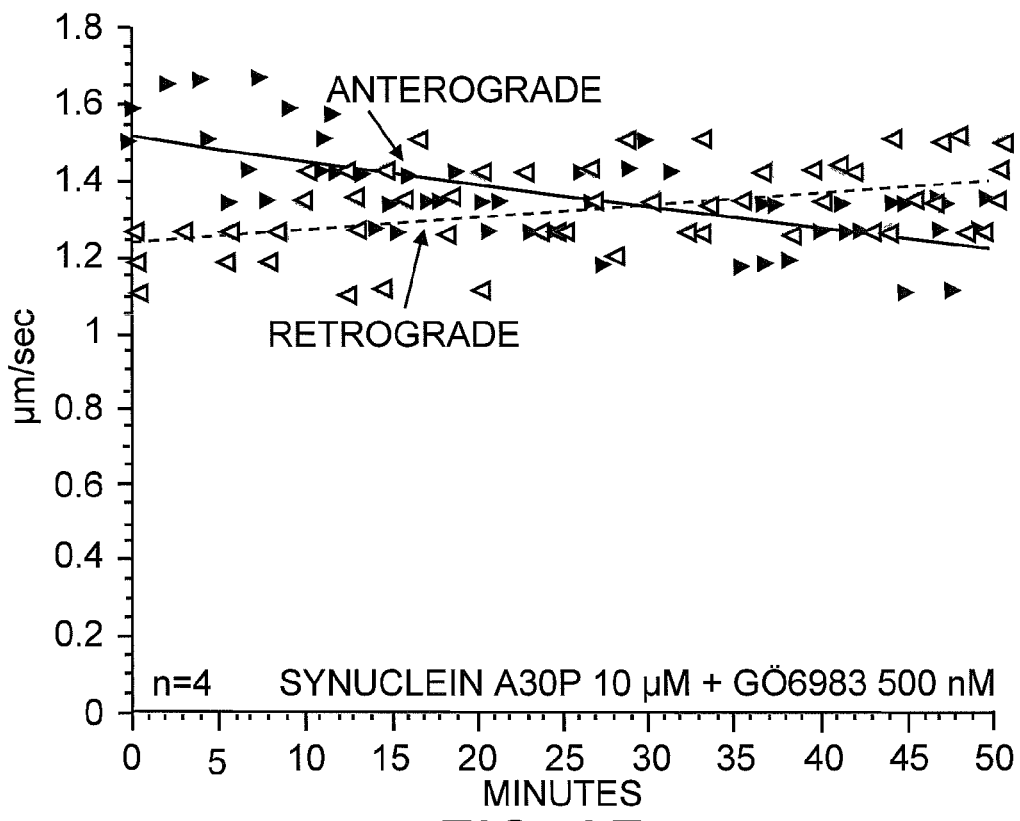

To demonstrate the involvement of Src-Family Nonreceptor Tyrosine Kinases and PKC, selective inhibitors were employed. Gö6976 is a broad spectrum inhibitor of PKC family kinases that also inhibits PKCmu. Gö6983 is a closely related compound that inhibits all PKC family members ($IC_{50}$=7 nM for PKCα and PKCβ; 6 nM for PKCγ; 10 nM for PKCδ; 60 nM for PKCζ), however, because this compound does not effectively inhibit PKCμ ($IC_{50}$=20 μM), it is routinely used to differentiate PKCμ from other isoforms. Accordingly, these inhibitors were coperfused with pathological α-synuclein mutant Ala30Pro and fast axonal transport was monitored. This analysis showed that Gö6976 prevented the effects of pathological synuclein on fast axonal transport (FIG. 3A) and neurotransmission. Similarly, the effects of α-synuclein mutant Ala30Pro could be blocked by a PKCmu peptide substrate (FIG. 3B) and an inhibitor of Src-Family Tyrosine Kinases (PP2) (FIG. 3C). In contrast, inhibitors of Caspase 3 (FIG. 3D) or PKCdelta (PKCdelta peptide substrate, FIG. 3E; and Gö6983, FIG. 3F) were not effective at blocking the effects of α-synuclein mutant Ala30Pro on fast axonal transport or neurotransmission.

Collectively, these data demonstrate that PKCmu and a Src-Family Tyrosine Kinase mediate the pathological effects of mutant α-synuclein on fast axonal transport. Conversely, PKCdelta and Caspase 3 do not play a role in the pathological effects of α-synuclein on axonal transport or neurotransmission.

Example 5

Modulation of Fast Axonal Transport by LB Filaments

Figure 4A:
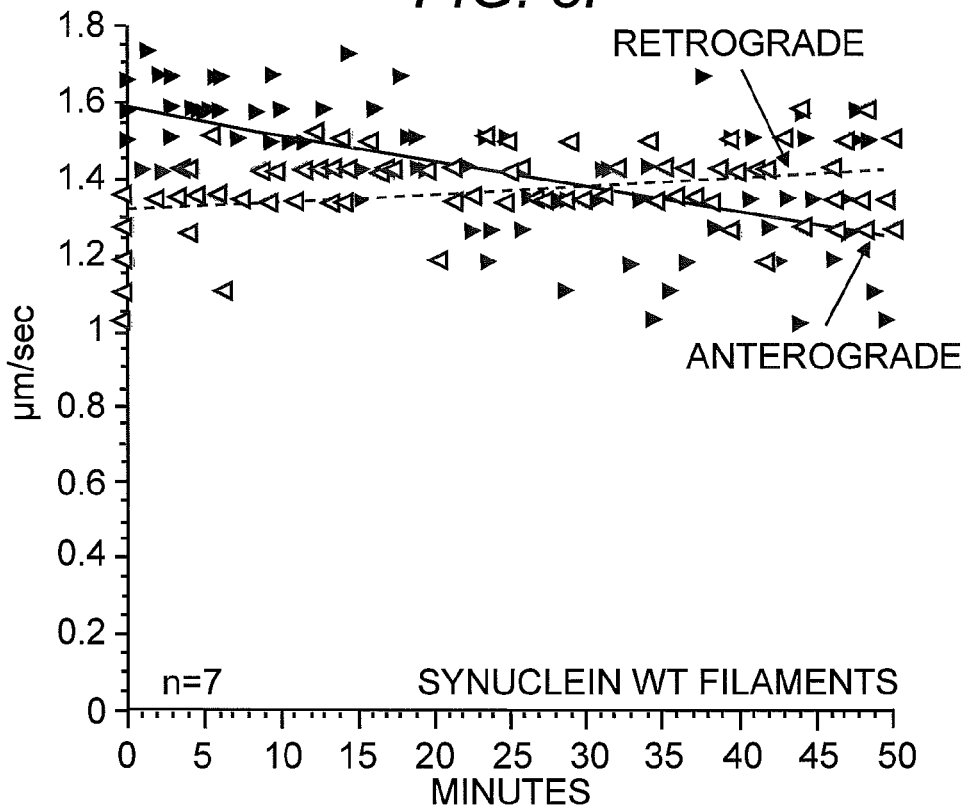
FIG. 4 shows that Lewy body filaments made from wild-type α-synuclein have the same effect as familial Parkinson's disease mutant forms. RT was activated and AT was inhibited (FIG. 4A). The effect of wild-type α-synuclein filaments was blocked by the PKC inhibitor Gö6976 (FIG. 4B).
Figure 4B:
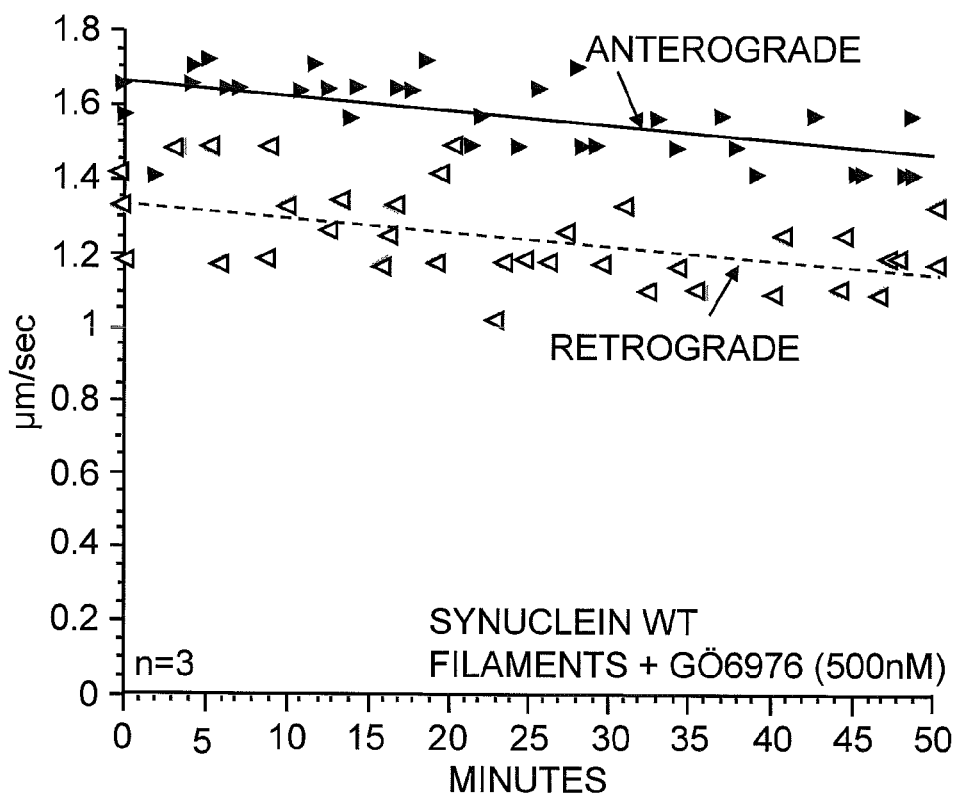

As with tau in Alzheimer's disease, recombinant wild-type α-synuclein can be induced to form filaments in vitro like those found in LB in vivo (Necula, et al. (2003) *J. Biol. Chem.* 278:46674-80). In vitro-assembled α-synuclein filaments are referred to herein as LB filaments, as the critical component α-synuclein is present. Soluble, wild-type α-synuclein had no effect on fast axonal transport (FIG. 2A), but LB filaments assembled from wild-type α-synuclein affect fast axonal transport in a manner similar to mutant α-synucleins (FIG. 4A). Specifically, in the presence of LB filaments, retrograde transport increased to 1.43±0.023 μm/sec (compared to 1.2 μm/sec in controls) and anterograde transport was reduced to 1.369±0.029 μm/sec (compared to 1.6 μm/sec in controls). The PKC inhibitor Gö6976 (FIG. 4B) and Src-family nonreceptor tyrosine kinase inhibitor PP2 blocked the effects of LB filaments on fast axonal transport much as they blocked the effects of mutant α-synucleins on fast axonal transport. As LB filaments are a hallmark of sporadic Parkinson's disease, these results indicate a role for pathogenic forms of α-synuclein in sporadic as well as familial forms of Parkinson's disease.

The effects of mutant α-synuclein and wild-type α-synuclein LB filaments in increasing retrograde transport and decreasing anterograde transport would reduce availability of essential synaptic components and return of neurotrophins to affected cell bodies. Thus, signaling by α-synuclein leads to distinct deleterious alterations of fast axonal transport that compromise neuronal function and viability.

Example 6

Fast Axonal Transport in Toxin-Induced Parkinson's Disease

Figure 5A:
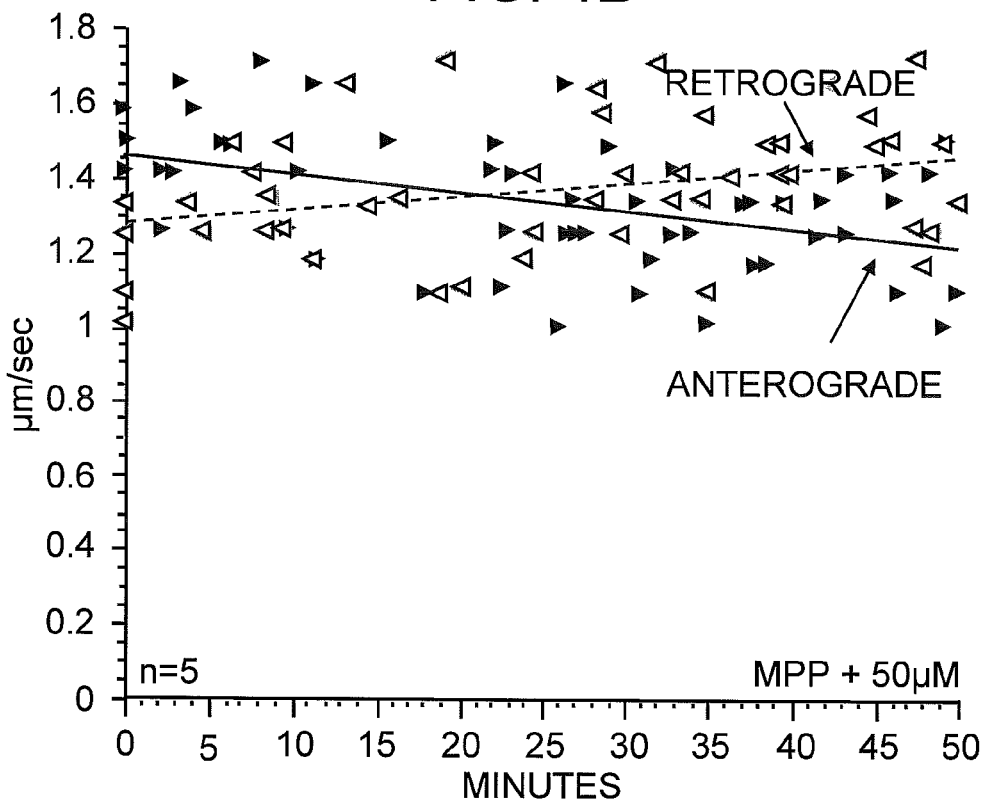
FIG. 5 shows that the toxic metabolite of MPTP, MPP+, affects fast axonal transport in a manner similar to familial Parkinson's disease α-synucleins and LB filaments (FIG. 5A). The effect of MPP+ was blocked by Gö6976 (FIG. 5B), but unlike pathogenic α-synucleins, MPP+ effects were also blocked by caspase3 inhibitor II, Gö6983 and a peptide substrate specific for PKCδ, but not by a peptide specific for PKCμ. Thus, MPP+ has a convergent pathogenic pathway that involves caspase 3 instead of Src-Family Tyrosine Kinases and MPP+ activates a different PKC isoform (PKCδ) that is inhibited by both Gö6983 and Gö6976 (Morfini, et al. (2007) Proc. Natl. Acad. Sci. USA 104:2442-2447); Serulle, et al. (2007) Proc. Natl. Acad. Sci. USA 104:2437-2441).
Figure 5B:
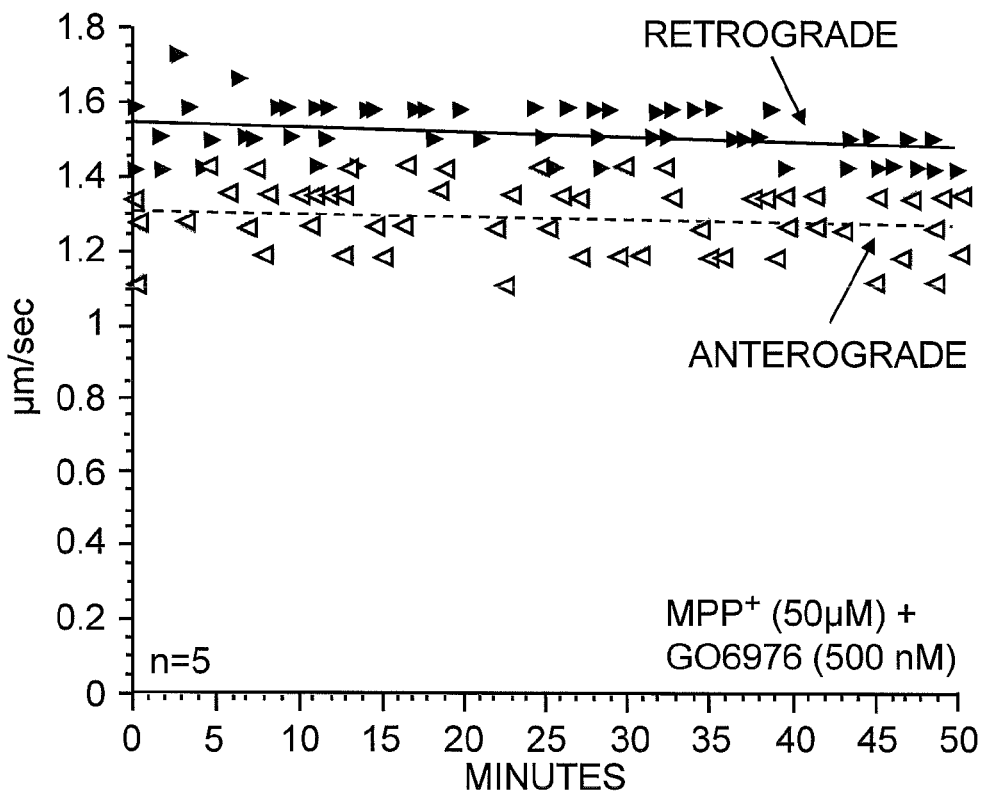

MPTP/MPP+ is the best characterized example of toxin-induced Parkinson's disease. The effects of MPP+ on fast axonal transport were examined in axoplasm as was dynein phosphorylation in cells. The results of this analysis indicated that MPP+ perfused into isolated axoplasm increased retrograde transport to 1.461±0.023 μm/sec and reduced anterograde transport to 1.272±0.0032 μm/sec (FIG. 5A) (Morfini, et al. (2007) supra), comparable to effects of PKC, Fyn, familial Parkinson's disease mutant α-synuclein and wild-type LB filaments. The Gö6976 inhibitor of PKC blocked the effect of MPP+ (FIG. 5B), but the PP2 tyrosine kinase inhibitor did not. MPP+ did not appear to involve a tyrosine kinase pathway. Based on reports that MPP+ could activate caspase3 (Turmel, et al. (2001) Mov. Disord. 16:185-9) and that caspase3 can activate a PKC by proteolytic cleavage (Kaul, et al. (2003) Eur. J. Neurosci. 18:1387-401), the ability of a caspase3 inhibitor to block effects of MPP+ on fast axonal transport was evaluated. This analysis showed that Caspase3 Inhibitor II (Calbiochem) could completely block the effects of MPP+ on fast axonal transport (retrograde transport=1.187±0.019 μm/sec and anterograde transport=1.527±0.019 μm/sec). Further, perfusion with Caspase 3 affected retrograde transport in a manner similar to PKC and MPP+ (retrograde transport=1.462±0.016 μm/sec). Consistent with this observation, labeling studies with MPP+ treated cortical neurons exhibited an increased DIC phosphorylation that was blocked by Caspase3 Inhibitor or Gö6976 and MPP+ activated PKC activity in axoplasm. These results indicate that pathogenic mechanisms for mutant α-synucleins, wild-type LB filaments, and MPP+ converge at the level of retrograde transport in neurons, but differ at higher levels in terms of the PKC isoform that is activated and the upstream pathways for activation of PKCs.

Example 7

Biological Effects of α-Synucleins

Having demonstrated the effects of pathologic α-synucleins on fast axonal transport, it was subsequently determined whether mutant α-synucleins and MPP+ had any effect on synaptic function (Serulle, et al. (2007) supra). If they both work by activating PKC and increasing retrograde transport, they might affect availability of synaptic vesicle components in presynaptic terminals. Accordingly, either wild-type α-synuclein, Ala30Pro α-synuclein, or MPP+ were injected into the presynaptic side of the squid giant synapse as described for synaptic vesicles and synapsin (McGuinness, et al. (1989) J. Neurosci. 9:4138-4149; Llinas, et al. (1989) Proc. Nat. Acad. Sci. USA 86:5656-5660). This preparation has been used to evaluate the effects of reagents on presynaptic function by injecting, then stimulating the presynaptic side while recording intracellularly on both pre- and post-synaptic sides (Llinas, et al. (2004) Proc. Natl. Acad. Sci. USA 101:17855-60; Sugimori, et al. (1998) Neuroscience 86:39-51). Injection of soluble, wild-type α-synuclein or vehicle had no effect on neurotransmission for up to 90 minutes, but the effect of injecting either Ala30Pro mutant α-synuclein or MPP+ led to a failure of neurotransmission and a block of the postsynaptic response after ≥30 minutes. The failure of neurotransmission was prevented by co-injection of an inhibitor that could block the effect of Ala30Pro mutant α-synuclein (PP2) or MPP+ (Caspase3 inhibitor II and PKCδ substrate peptide) on retrograde transport.

Figure 6A:
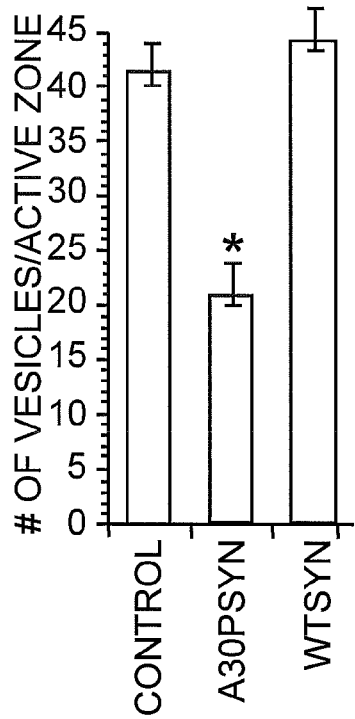
FIG. 6 shows changes in vesicle number and distribution in synapses injected with Ala30Pro or wild-type α-synucleins. Morphometric analysis of vesicles at active zones at the giant synapse showed a reduction in vesicle number. Synapses were injected with Ala30Pro or wild-type α-synuclein and evaluated by electrophysiology, then processed for electron microscopy (EM). Ala30Pro, but not wild-type α-synuclein, exhibited a failure of neurotransmission without recovery. Ala30Pro α-synuclein (A30PSyn) injected synapses exhibited significantly fewer total vesicles (FIG. 6A), docked vesicles (FIG. 6B), and clathrin-coated vesicles (FIG. 6C) per active zone than either unstimulated (Control) or wild-type αsynuclein (WTSyn) injected synapses (p≤0.01).
Figure 6B:
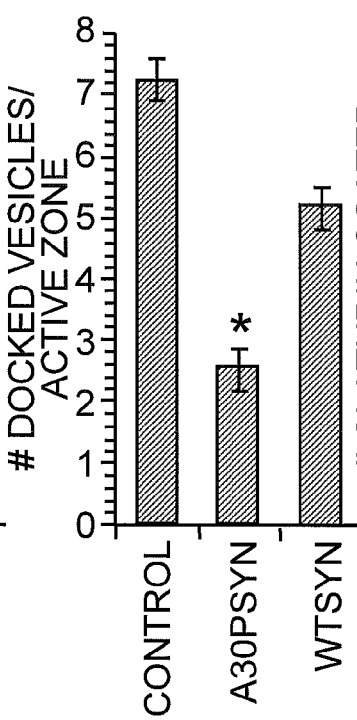
Figure 6C:
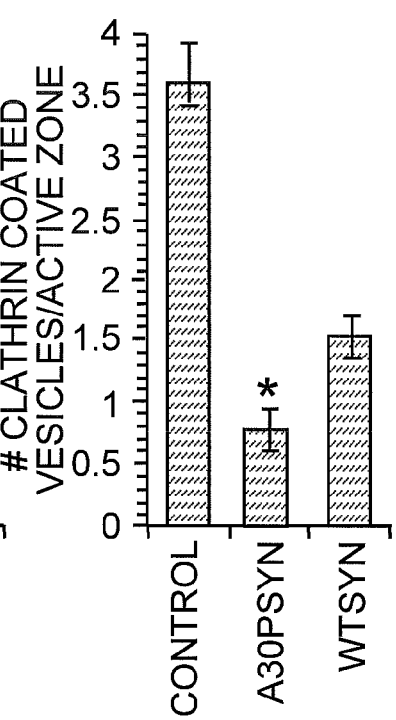

Synapses injected with either MPP+ or Ala30Pro mutant α-synuclein exhibiting a failure of neurotransmission were processed for EM morphometry along with paired synapses injected with wild-type α-synuclein according to established methods (Llinas, et al. (2004) supra; Marsal, et al. (1997) Proc. National Acad. Sci. USA 94:14871-14876). Presynaptic terminals injected with vehicle or with either wild-type or Ala30Pro mutant α-synuclein exhibited normal size and overall morphology, but presynaptic terminals injected with Ala30Pro mutant α-synuclein were significantly depleted of synaptic vesicles relative to control and wild-type α-synuclein injections. Proportional changes were noted in total vesicles (FIG. 6A), docked vesicles (FIG. 6B) and clathrin-coated vesicles (FIG. 6C) per active zone. Both failure of neurotransmission and the absence of synaptic vesicles are consistent with an activation of retrograde transport that depletes presynaptic terminals of membrane-bounded organelles and compromises neuronal function. Taken together, these results indicate a novel pathogenic mechanism for loss of nigral dopaminergic neurons in Parkinson's disease; pathological forms of α-synuclein alter normal regulation of fast axonal transport and compromise neuronal function.

Not wishing to be bound by theory, it is contemplated that normal pathways for regulating fast axonal transport through one or more PKC isoforms are altered by increases in local PKC activities and results in a premature return of vesicles to the cell body. This reduces the availability of synaptic components for neurotransmitter release as well as affecting return of neurotrophins. As a result, release of synaptic function of dopaminergic neurons is reduced and eventually synaptic function is lost, triggering a dying back neuropathy and eventual death of affected neurons.

What is claimed is:

1. A method for restoring fast axonal transport in a cell which expresses a pathological synuclein protein comprising contacting the cell with an effective amount of an agent that inhibits Protein Kinase C mu or Src-Family Tyrosine Kinase activity and measuring PKC mu or Src-Family Tyrosine Kinase activity, thereby restoring fast axonal transport in the cell, wherein said agent that inhibits Protein Kinase C mu comprises Gö6976, MARCKS peptide, or PKC mu peptide substrate and said agent that inhibits Src-Family Tyrosine Kinase comprises PP2, PP1, Radicicol R2146, Geldanamycin, Herbimycin A, PD173955, SKI-606, or PD162531.

2. A method for treating a synucleinopathy comprising administering to a subject with a synucleinopathy an effective amount of Protein Kinase C mu or Src-Family Tyrosine Kinase inhibitor wherein said Protein Kinase C mu inhibitor comprises Gö6976, MARCKS peptide, or PKC mu peptide substrate and said Src-Family Tyrosine Kinase inhibitor comprises PP2, PP1, Radicicol R2146, Geldanamycin, Herbimycin A, PD173955, SKI-606, or PD162531, and measuring PKC mu or Src-Family Tyrosine Kinase activity thereby treating the synucleinopathy.

3. The method of claim 2, wherein the synucleinopathy is Parkinson's disease.

* * * * *